United States Patent
Biel et al.

(10) Patent No.: US 7,339,171 B2
(45) Date of Patent: Mar. 4, 2008

(54) METHOD AND APPARATUS FOR DETECTING PRESENCE OF AN OPHTHALMIC LENS IN A PACKAGE

(75) Inventors: Roger Biel, Aschaffenburg (DE); Torsten Gruhn, Teningen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/653,571

(22) Filed: Jan. 16, 2007

(65) Prior Publication Data

US 2007/0164222 A1 Jul. 19, 2007

(30) Foreign Application Priority Data

Jan. 17, 2006 (EP) ............................... 06000926

(51) Int. Cl.
G01F 23/00 (2006.01)
(52) U.S. Cl. .................................. 250/358.1
(58) Field of Classification Search ............. 250/358.1, 250/338.1, 338.2, 338.3, 338.4, 338.5, 339.01, 250/339.02, 339.03, 339.04, 339.05, 33.06, 250/339.07, 339.08, 339.1, 339.11, 339.12, 250/339.13, 339.14, 339.15, 340, 341.1, 250/341.2, 341.3, 341.5, 341.6, 341.7, 341.8, 250/350, 360.1, 370.01, 370.02, 370.03, 250/370.04, 370.05, 370.06, 370.07, 370.08, 250/370.09; 250/370.1, 370.11, 370.12, 250/370.13, 370.14, 370.15
See application file for complete search history.

(56) References Cited

U.S. PATENT DOCUMENTS

| 2003/0205672 A1 | 11/2003 | Duggan et al. ........... 250/341.8 |
| 2004/0036858 A1 * | 2/2004 | Biel et al. .................... 356/124 |
| 2007/0121181 A1 * | 5/2007 | Moon et al. ..................... 359/2 |
| 2007/0122540 A1 * | 5/2007 | Salamone et al. .......... 427/2.24 |
| 2007/0145616 A1 * | 6/2007 | Vanderlaan et al. .......... 264/2.6 |

FOREIGN PATENT DOCUMENTS

| EP | 0 685 734 A1 | 12/1995 |
| EP | 1 050 470 A1 | 11/2000 |
| EP | 1 057 730 A1 | 12/2000 |
| EP | 1 109 011 A1 | 6/2001 |
| EP | 0 999 140 B1 | 9/2005 |
| JP | 2003-267326 | 9/2003 |
| JP | 2005-121368 | 5/2005 |

OTHER PUBLICATIONS

PCT International Search Report.
PCT Written Opinion of the International Searching Authority.
US 4,514,954, 05/1985, Anderson et al. (withdrawn)

* cited by examiner

*Primary Examiner*—Kiesha Rose
*Assistant Examiner*—Kiho Kim
(74) *Attorney, Agent, or Firm*—Sheng-Hsin Hu; Robert Ambrose

(57) ABSTRACT

The invention relates to a method and apparatus for detecting the presence of an ophthalmic lens, particularly a contact lens, in a package. The method for detecting the presence of an ophthalmic lens, particularly a contact lens, in a package, is characterised in that the package is checked for presence of an ophthalmic lens with an x-ray detection system and with an optical detection system, whereby presence of an ophthalmic lens is given if either one or both cameras detect presence of an ophthalmic lens.

10 Claims, 3 Drawing Sheets

METHOD AND APPARATUS FOR DETECTING PRESENCE OF AN OPHTHALMIC LENS IN A PACKAGE

This application claims benefit under 35 USC §119 of European Application No. EP 06000926.3 filed 17 Jan. 2006, the contents of which are incorporated herein by reference.

BACKGROUND OF THE INVENTION

The invention relates to a method and apparatus for detecting the presence of an ophthalmic lens, particularly a contact lens, in a package. The method for detecting the presence of an ophthalmic lens, particularly a contact lens, in a package, is characterised in that the package is checked for presence of an ophthalmic lens with an x-ray detection system and with an optical detection system, whereby presence of an ophthalmic lens is given if either one or both cameras detect presence of an ophthalmic lens.

Ophthalmic lenses are usually placed in a package for storage and for transport. The preferred packages are so-called blister packages. A blister package consists of a plastic container, for example made of polypropylene (PP), the top of which is sealed with a film (plastic or composite material) after the ophthalmic lens has been placed in the plastic container.

In particular, contact lenses that are produced in large unit numbers, for example disposable contact lenses, are sealed into blister packages. Such contact lenses are preferably manufactured by fully automated so-called mould or full-mould processes. The contact lenses produced in this manner are moulded parts usually having little mechanical stability and a water content of more than 60% by weight. After manufacture, the lens is usually checked for defects, then packaged and subjected to heat sterilisation at 121° C. in an autoclave.

Under certain circumstances, empty packages may appear in the process. Without checking the presence of a contact lens in each package, an empty package may be delivered to the customer, which is considered a serious quality issue in a competitive market situation. Empty packages in the process may be recognised by chance or by spot checks, with the result, that either the whole batch has to be rejected or all the contact lens packages of the batch have to undergo manual checking. Both procedures involve substantial costs and effort.

The following technical solutions are known for detecting the presence of an ophthalmic lens, particularly a contact lens, in a package:

EP0685734 A discloses a method and system for verifying the presence of a lens in a transparent package. The method comprises the steps of moving the package into an inspection position, and conducting a light beam through the package and onto an image plane to form an image of the package on the image plane. The method further comprises the steps of generating a set of signals representing the image on the image plane, and analyzing those signals to determine whether a lens is present in the package. This analyzing step includes the steps of searching the package image for images of discrete objects and for each object image found in the package image, identifying values for a plurality of parameters, and analyzing those identified values according to a predetermined procedure to identify the object as being a lens or as not being a lens. A lens present signal is generated if one object image found in the package image is identified as a lens and a lens missing signal is generated if no object images are found in the package image or if all object images found in the package image are identified as not lenses.

EP0999140 B1 discloses an apparatus for detecting the presence or position of an ophthalmic lens, such as a contact lens in saline solution, in a container using a source of electromagnetic energy in the ultraviolet range. The source of electromagnetic enemy is located relative to the container to direct ultraviolet electromagnetic energy at the container. A detector is disposed relative to the container and the source to detect the electromagnetic energy from the source which is reflected by the lens and the container. A processor is included for determining the presence or position of the lens in the container responsive to the reflection of the ultraviolet electromagnetic energy by the lens.

EP1050470 A discloses a method and a device for detecting the presence of an ophthalmic lens, particularly a contact lens, in a package. The method uses a spectroscopic process. Packages containing a contact lens have a characteristic change in their measuring spectrum compared with a package without a contact lens. By evaluating the spectra, it is possible to determine whether or not there is a contact lens in a package. The method is suitable for checking already sealed packages with the packages remaining intact.

EP1057730 A discloses a method and a device for detecting the presence of an ophthalmic lens using electromagnetic radiation of a characteristic resonance frequency of atomic groups within the object (e.g. a contact lens), in particular using near infrared radiation (NIR).

EP1109011 A discloses a method and a device for registering the presence of an ophthalmic lens, particularly a contact lens in a package. The invention solves the problem through the use of an IR camera. Packages containing a contact lens, have a change in their temperature distribution compared with a package without a contact lens. By evaluating the temperature difference directly after the procedure for filling the lens into the package, it is possible to determine whether or not there is a contact lens in a package.

JP2003267326 and JP2005121368 disclose a method capable of automating and highly accurately implementing the detection of the presence or absence of ophthalmic lenses in a housing case, the number of present ophthalmic lenses, or their types without visual inspection with human eyes. The housing case to be detected is irradiated with inspecting light of the visible light region, and transmitted light or reflected light from the housing case is imaged by a color image sensor. The presence or absence of colored ophthalmic lenses in the housing case, the number of present ophthalmic lenses, or their types are determined based on acquired R values, G values, and B values.

There are several draw backs to the methods known in the art for detecting the presence of an ophthalmic lens, particularly a contact lens, in a package. Optical detection systems, in particular in the ultraviolet or visible range of electromagnetic radiation, are suitable to detect slightly wet or dry lenses very reliable, but often fail to detect wet lenses. It is particularly difficult to differentiate between a drop of water and a wet lens in a package. Temperature systems, in particular in the infrared or near infrared range of electromagnetic radiation require extensive calibration to be reliable. Finally, imaging systems require a rather complex logical setup for reliable detection, as for each object image found in the total package image, values for a plurality of parameters have to be identified and analyzed according to a predetermined procedure to identify the object as a lens or as not a lens.

The invention is therefore based on the problem of providing a reliable and simple testing method with which it is possible to detect, at low cost and with a limited logical setup, whether an ophthalmic lens, especially a contact lens, is actually present in a package. Such method should be reliable for wet, slightly wet as well as for dry lenses.

SUMMARY OF THE INVENTION

The invention solves this problem with the features indicated in claim 1, in which is claimed a method for detecting the presence of an ophthalmic lens, particularly a contact lens, in a package, the method characterised in that the package is checked for presence of an ophthalmic lens with an optical detection system and with an x-ray detection system. As far as further essential refinements are concerned, reference is made to the dependent claims.

BRIEF DESCRIPTION OF THE DRAWINGS

Further details and advantages of the invention may be seen from the drawings.

DETAILED DESCRIPTION OF THE INVENTION

A "contact lens" refers to an object that can be placed on or within a wearer's eye. A contact lens can correct, improve, or alter a user's eyesight, but that need not be the case. A contact lens can be a soft lens, a hard lens, or a hybrid lens. A contact lens can be in a dry state or a wet state. "Dry" state refers to a soft lens in a state prior to hydration or the state of a hard lens under storage or use conditions. "Wet" state refers to a soft lens in a hydrated state. Preferably a wet lens has a water content of more than 30%, more preferably of more than 45%, most preferably a water content of more than 60% by weight.

A "slightly wet" lens in terms of the present invention is a lens with a water content of less than 30% by weight or a lens which is wet only on the surface.

"Saline" is a term generally known in the art. In particular "saline" is a solution of salt (e.g. NaCl) in purified or distilled water, mimicking the tear fluid. "Saline" preferably is buffered saline, most preferably phosphate buffered saline (PBS).

A "detection system" in terms of the present invention comprises an emitter for electromagnetic radiation of the respective wavelength as well as a camera. A "camera" in terms of the present invention is a detector for electromagnetic radiation of the respective wavelength. e.g. an x-ray camera for electromagnetic radiation in the x-ray spectrum or a CCD camera for electromagnetic radiation in the visible spectrum.

A "line camera" in terms of the present invention is a camera, wherein the detector is a linear device, with a line resolution of preferably 128 pixels.

Surprisingly, it has been found that the combination of an x-ray detection system and an optical detection system allows the reliable detection of a presence of an ophthalmic lens, particularly a contact lens, in a package. In particular the use of an x-ray detection system improves the detection of "wet" contact lenses compared to methods known in the art.

Figure 1:
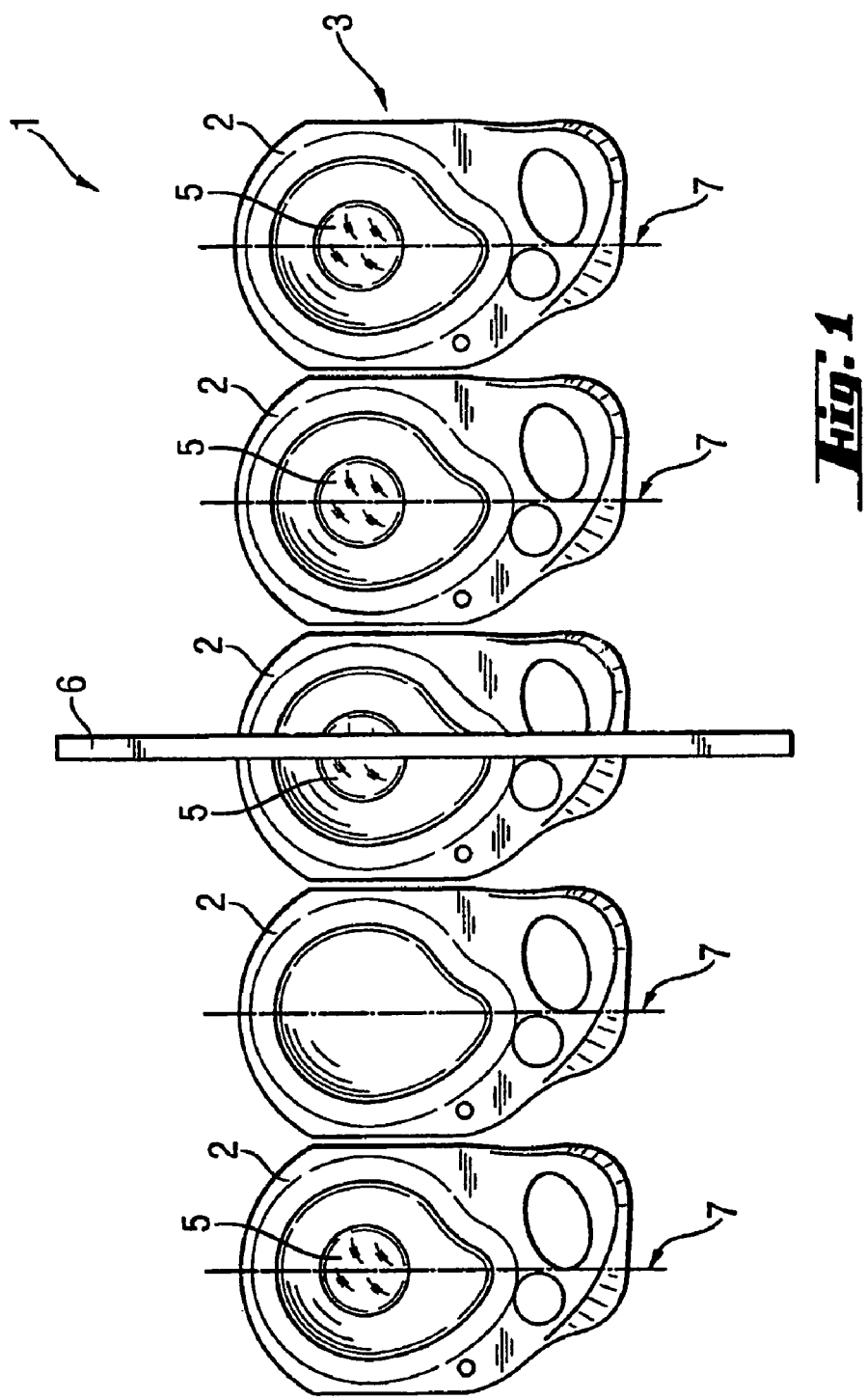
FIG. 1 shows a schematic illustration of an embodiment of a checking device according to the invention.

In FIG. 1, a checking device 1 according to the invention is illustrated. The checking device 1 is preferably integrated into a packaging appliance, not illustrated here, in such a way that it is possible to detect the presence of a contact lens 5 in the package during the production process. FIG. 1 shows a schematic illustration of a packaging unit 3 comprising five blister containers 2, arranged in series, which in the production process are transported continuously by an appliance, as for example illustrated schematically in FIG. 3, on a tool holder 4, as for example illustrated schematically in FIGS. 2 and 3. The blister containers 2 are usually joined together by a film cover (not illustrated here to form a blister strip. The outline of the film cover corresponds to the contour of the top of the blister containers 2, since when the object to be packaged, preferably a contact lens 5, has been inserted, the film cover is heat-sealed to each blister container 2 individually. Prior to applying the film cover or after applying and sealing the film, however, there is a provision according to the invention for checking whether each of the blister containers 2 contains a contact lens 5.

Figure 2:
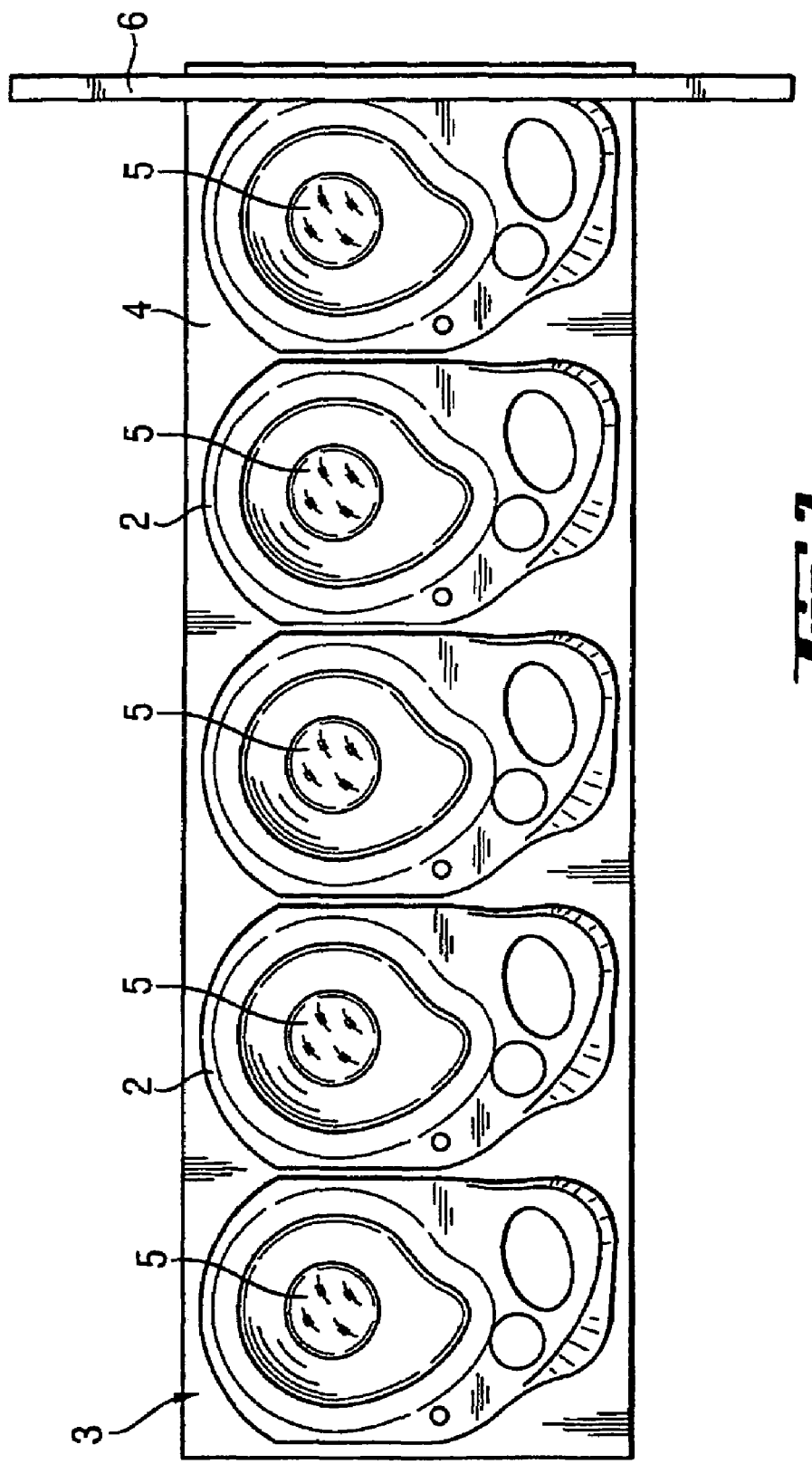
FIG. 2 shows a schematic illustration of an embodiment of a checking device according to the invention.

In a first part, the checking device 1 of FIG. 1 and FIG. 2 comprises an x-ray detection system comprising an x-ray line camera 6. Further, in a second part, the checking device 1 of FIG. 1 and FIG. 2 comprises an optical camera not illustrated here.

Figure 3:
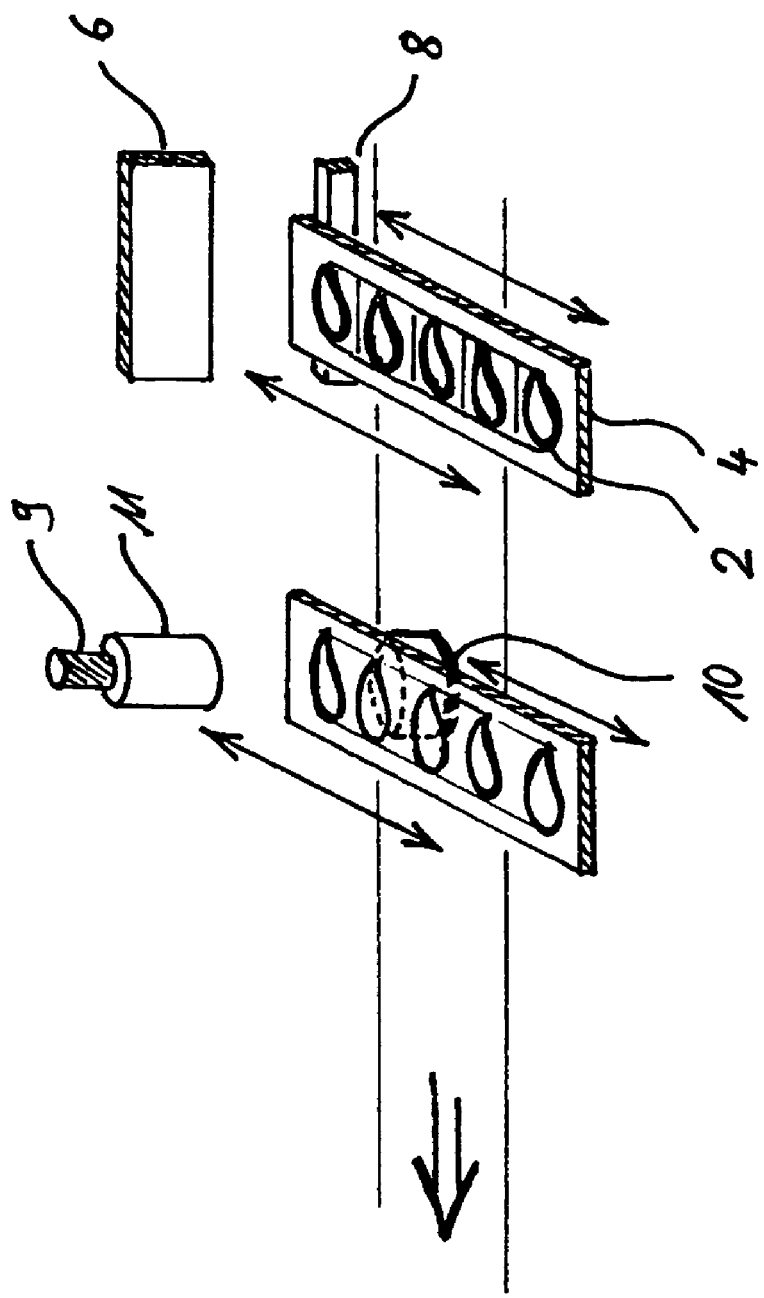
FIG. 3 shows a schematic illustration of a preferred embodiment of a checking device according to the invention.

In a preferred embodiment as shown in FIG. 3, a complete checking apparatus according to the invention comprises both, a first detection system with an x-ray line camera 6 and an x-ray source 8, as well as a second detection system with an optical camera 9, optionally an appropriate lens 11, and a light source 10.

The optical camera preferably is a CCD camera with an area resolution of 768×1024 pixels at 30 fps. The light source preferably is a LED condenser illumination. Most preferably the light source is a LED condenser illumination with integrated flash mode. The x-ray line camera preferably has a line resolution of 128 pixels.

As shown in FIG. 3 the detection systems are preferably arranged above or below the tool holder 4. Further, as schematically indicated in FIG. 3, the detection systems are moved back and forth over the packages in the tool holder 4 in a scanning type motion. In a preferred embodiment, the tool holder 4 is stopped for lens detection such that the midline 7 (FIG. 1) of each blister container 2 is stopped in the measuring area of each of the detection systems. More preferably the detection systems are moved by the same actuation means in a simultaneous scanning type motion.

The two detection systems may arranged in a way that they scan the same package simultaneously, or they may be arranged to scan the same package subsequently, preferably in two different measuring areas (one for each detection system). To allow the both systems to be moved by the same actuation means in a simultaneous scanning type motion in said second arrangement, the movement of two subsequent packages have to be synchronized in the two different measuring areas. In an alternative embodiment, the two subsequent packages have to be stopped in the two different measuring areas each by a stopper.

The repeat rate of the measurements in respect of a blister container is advantageously very high, so that the cameras are preferably in continuous operation. In this way, a high degree of certainty can be achieved in respect of the measurement results.

The checking device is advantageously equipped with an integrated electronic evaluation means. Through an intersection, the checking device can be connected to the machine control of the packaging appliance, not illustrated here. However, it is also conceivable for the evaluation signals from the checking device to be passed directly to a PC control unit of the appliance (not illustrated here).

Preferably, the software for control of the checking devices and evaluation of the signals from the checking devices allows to process the results of measurement from both cameras. If one or both cameras detect a contact lens, this means that a contact lens is present in the package. If neither the optical camera nor the x-ray camera detects a contact lens, this means that no contact lens is present in the package. Said package can than be rejected.

As is also evident the packaging appliance is advantageously equipped with a sensor (not shown) which detects when a tool holder 4 mounted with the package 3 reaches each of the measuring areas. Such a sensor can record when a tool holder 4 leaves and/or enters the measuring areas. Thus, it is not necessary to incorporate series of stoppers or other synchronisation measures.

Of course it is also possible to design the checking system independently of a blister strip consisting of five blister packages, and to undertake individual detection and processing.

In a first general aspect, the invention is directed to a method for detecting the presence of an ophthalmic lens, particularly a contact lens, in a package, characterised in that the package is checked for presence of an ophthalmic lens with an optical detection system and with an x-ray detection system.

Preferably, the method comprises the following steps: first checking a package for presence of an ophthalmic lens with an x-ray detection system; then checking said package for presence of an ophthalmic lens with an optical detection system.

More preferably the method comprises the step of combining the results of the checking said package for presence of an ophthalmic lens with an x-ray detection system and of the checking said package for presence of an ophthalmic lens with an optical detection system, whereby presence of an ophthalmic lens is given if either one or both results detect presence of an ophthalmic lens.

In one preferred aspect of the method according to the invention the package is checked subsequently by the two detection systems, while the package is kept in the same position. In another preferred aspect of the method according to the invention the package is checked simultaneously by the two detection systems, while the package is kept in the same position. In a most preferred aspect of the method according to the invention the package is checked subsequently by the two detection systems, while the package is checked by the first system in a first position and by the second system in a second position.

The method according to the invention may be used to detect the presence of an ophthalmic lens, particularly a contact lens, in a package, preferably in a blister container, prior to applying a film or after applying and sealing the film. Most preferably the method is used to detect the presence of an ophthalmic lens, particularly a contact lens, in an open package, i.e. prior to applying and sealing the film. In a preferred embodiment of the invention, the presence check is performed before the package is filled with saline solution, i.e. with the "dry" package.

In a second general aspect the invention is directed to an apparatus for detecting ophthalmic lenses, particularly contact lenses, in a package, particularly a blister package, wherein the apparatus comprises an x-ray detection system for detecting an ophthalmic lens and an optical detection system for detecting an ophthalmic lens.

In a preferred embodiment, the x-ray detection system comprises an x-ray line camera, with a line resolution of preferably 128 pixels.

Preferably, the apparatus further comprises a sensor for detecting when a package enters and/or leaves the measuring area of the detection systems.

More preferably the apparatus comprises an electronic evaluation means, which is capable of combining the results of detecting an ophthalmic lens in a package by an x-ray detection system and the results of detecting an ophthalmic lens in a package by an optical detection system, and rejecting the package if neither the optical detection system nor the x-ray detection system detects an ophthalmic lens.

Moreover, there may advantageously be a provision for the package detected as being empty to be automatically removed from the packaging appliance.

EXAMPLES

The following tests carried out by way of example were effected using a checking device according to FIG. 3 comprising a first detection system with an optical camera (VIS camera) and a second detection system with an x-ray line camera (X-ray camera):

Example 1

"Dry" Lenses in Open Packages with "Dry" Empty Packages Randomly Distributed

50% "dry" empty packages were produced, i.e. not containing a contact lens (CL) in one of the five blister containers of a blister strip (e.g. a situation as shown in FIG. 1). All blister containers were "dry" blister containers, i.e. not containing saline solution. Further, the "dry" empty packages were not containing any saline solution or any drop of water.

"Dry" lenses for the purpose of this test are soft contact lenses prior to hydration or "slightly wet" lenses with a water content of less than 30% by weight or a lens which is wet only on the surface.

The "dry" empty packages were randomly distributed among the tool holders. An evaluation was made by making a comparison between a manual inspection and the combined results of the contact lenses detected by the two cameras.

Test results:

| | VIS camera | X-ray camera | manual inspection | combined consistency |
|---|---|---|---|---|
| CL present | 360 | 390 | 360 | |
| CL not present | 40 | 10 | 40 | 100% |
| total | 400 | 400 | 400 | |

The test shows that the presence of contact lenses is detected at a rate of 100% by the combination of the two cameras. There was not a single case in which neither the one nor the other camera had not noticed the absence of a lens. The test further shows, that the X-ray camera alone would not provide consistent results for "dry" empty packages with "dry" lenses. The combination of the two cameras thus enables fault-free detection to be made of contact lenses in a package.

Example 2

"Wet" Lenses in Open Packages with "Dry" Empty Packages Randomly Distributed

50% "dry" empty packages were produced, i.e. not containing a contact lens (CL) in one of the five blister containers of a blister strip (e.g. a situation as shown in FIG. 1). All blister containers were "dry" blister containers, i.e. not containing saline solution. Further, the "dry" empty packages were not containing any saline solution or any drop of water.

"Wet" lenses for the purpose of this test are soft contact lenses after hydration with a water content of at least 30% by weight.

The "dry" empty packages were randomly distributed among the tool holders. An evaluation was made by making a comparison between a manual inspection and the combined results of the contact lenses detected by the two cameras.

Test results:

|  | VIS camera | X-ray camera | manual inspection | combined consistency |
|---|---|---|---|---|
| CL present | 360 | 360 | 360 |  |
| CL not present | 40 | 40 | 40 | 100% |
| total | 400 | 400 | 400 |  |

The test shows that the presence of contact lenses is detected at a rate of 100% by the combination of the two cameras. There was not a single case in which neither the one nor the other camera had not noticed the absence of a lens. The test further shows, that for the specific test situation of only "dry" packages with or without "wet" lenses each camera alone would provide consistent results for empty packages.

Example 3

"Dry" Lenses in Open Packages with "Wet" Empty Packages Randomly Distributed

50% "wet" empty packages were produced, i.e. not containing a contact lens (CL) in one of the five blister containers of a blister strip (e.g. a situation as shown in FIG. 1). All blister containers were "dry" blister containers, i.e. not containing saline solution. However, the "wet" empty packages were containing up to 100 µl of water.

"Dry" lenses for the purpose of this test are soft contact lenses prior to hydration or "slightly wet" lenses with a water content of less than 30% by weight or a lens which is wet only on the surface.

The "wet" empty packages were randomly distributed among the tool holders. An evaluation was made by making a comparison between a manual inspection and the combined results of the contact lenses detected by the two cameras.

Test results:

|  | VIS camera | X-ray camera | manual inspection | combined consistency |
|---|---|---|---|---|
| CL present | 360 | 390 | 360 |  |
| CL not present | 40 | 10 | 40 | 100% |
| total | 400 | 400 | 400 |  |

The test shows that the presence of contact lenses is detected at a rate of 100% by the combination of the two cameras. There was not a single case in which neither the one nor the other camera had not noticed the absence of a lens. The test further shows, that the X-ray camera alone would not provide consistent results for "wet" empty packages with "dry" lenses. The combination of the two cameras thus enables fault-free detection to be made of contact lenses in a package.

Example 4

"Wet" Lenses in Open Packages with "Wet" Empty Packages Randomly Distributed

50% "wet" empty packages were produced, i.e. not containing a contact lens (CL) in one of the five blister containers of a blister strip (e.g. a situation as shown in FIG. 1). All blister containers were "dry" blister containers, i.e. not containing saline solution. However, the "wet" empty packages were containing up to 100 µl of water.

"Wet" lenses for the purpose of this test are soft contact lenses after hydration with a water content of at least 30% by weight.

The "wet" empty packages were randomly distributed among the tool holders. An evaluation was made by making a comparison between a manual inspection and the combined results of the contact lenses detected by the two cameras.

Test results:

|  | VIS camera | X-ray camera | manual inspection | combined consistency |
|---|---|---|---|---|
| CL present | 390 | 360 | 360 |  |
| CL not present | 10 | 40 | 40 | 100% |
| total | 400 | 400 | 400 |  |

The test shows that the presence of contact lenses is detected at a rate of 100% by the combination of the two cameras. There was not a single case in which neither the one nor the other camera had not noticed the absence of a lens. The test further shows, that the VIS camera alone would not provide consistent results for "wet" empty packages with "wet" lenses. The combination of the two cameras thus enables fault-free detection to be made of contact lenses in a package.

Example 5

Mixed Sample Set in an Automated Production Line

In a set up as described in examples 1 to 4, a mixed sample set of 1040 packages was tested under realistic conditions in an automated production line, wherein in the mixed sample set 123 no-lens packages were randomly distributed. All packages were either "dry" or "wet" packages, i.e. not containing saline solution. The lenses were either "dry" lenses or "wet" lenses.

RESULTS

The results were verified by manual inspection of all 1040 packages. The combination of the two cameras detected fault-free all 123 no-lens packages and all 917 packages with a contact lens present (consistency 100%).

The invention claimed is:

1. Method for detecting the presence of an ophthalmic lens, particularly a contact lens, in a package, characterised in that the package is checked for presence of an ophthalmic lens with an optical detection system and with an x-ray detection system.

2. Method according to claim 1, comprising the following steps:
   first checking a package for presence of an ophthalmic lens with an x-ray detection system; then checking said package for presence of an ophthalmic lens with an optical detection system.

3. Method according to claim 1, further comprising the step of:
   combining the results of the checking said package for presence of an ophthalmic lens with an x-ray detection system and of the checking said package for presence of an ophthalmic lens with an optical detection system, whereby presence of an ophthalmic lens is given if either one or both results detect presence of an ophthalmic lens.

4. Method according to claim 1, in which the package is checked subsequently by the two detection systems, while the package is kept in the same position.

5. Method according to claim 1, in which the package is checked simultaneously by the two detection systems, while the package is kept in the same position.

6. Method according to claim 1, in which the package is checked subsequently by the two detection systems, while the package is checked by the first system in a first position and by the second system in a second position.

7. Apparatus for detecting ophthalmic lenses, particularly contact lenses, in a package, particularly a blister package, wherein the apparatus comprises an x-ray detection system for detecting an ophthalmic lens and an optical detection system for detecting an ophthalmic lens.

8. Apparatus according to claim 7, in which the x-ray detection system comprises an x-ray line camera.

9. Apparatus according to claim 7 further comprising a sensor for detecting when a package enters and/or leaves the measuring area of the detection systems.

10. Apparatus according to claim 7 further comprising an electronic evaluation means, which is capable of combining the results of detecting an ophthalmic lens in a package by an x-ray detection system and the results of detecting an ophthalmic lens in a package by an optical detection system, and rejecting the package if neither the optical detection system nor the x-ray detection system detects an ophthalmic lens.

* * * * *